(12) United States Patent
Thorne

(10) Patent No.: US 8,206,355 B2
(45) Date of Patent: Jun. 26, 2012

(54) MEDICAL NEEDLE SAFETY SHIELD APPARATUS WITH AN ANTI-ROTATION MEMBER

(75) Inventor: David L Thorne, Kaysville, UT (US)

(73) Assignee: Specialized Health Products, Inc., Salt Lake City, UT (US)

( * ) Notice: Subject to any disclaimer, the term of this patent is extended or adjusted under 35 U.S.C. 154(b) by 360 days.

(21) Appl. No.: 11/492,679

(22) Filed: Jul. 25, 2006

(65) Prior Publication Data

US 2008/0097304 A1  Apr. 24, 2008

(51) Int. Cl.
  A61M 5/178 (2006.01)
  A61M 5/00 (2006.01)
  A61M 3/00 (2006.01)
  A61B 19/00 (2006.01)

(52) U.S. Cl. .......... 604/164.08; 604/110; 604/263; 604/192; 128/919

(58) Field of Classification Search .......... 604/110, 604/263, 164.08, 192; 128/919
See application file for complete search history.

(56) References Cited

U.S. PATENT DOCUMENTS

| 4,915,696 | A | * | 4/1990 | Feimer | 604/192 |
| 5,026,356 | A |   | 6/1991 | Smith | |
| 5,092,461 | A | * | 3/1992 | Adam | 206/365 |
| 5,152,751 | A | * | 10/1992 | Kozlowski | 604/192 |
| 5,312,372 | A |   | 5/1994 | DeHarde et al. | |
| 5,466,223 | A | * | 11/1995 | Bressler et al. | 604/110 |
| 6,716,199 | B2 | * | 4/2004 | DeHarde et al. | 604/263 |
| 7,077,824 | B2 | * | 7/2006 | Meyer | 604/110 |
| 2005/0182362 | A1 | * | 8/2005 | Sircom et al. | 604/110 |

OTHER PUBLICATIONS

Aug. 4, 2008, Written Opinion of the International Searching Authority in international application PCT/US2007/016395.
Aug. 4, 2008, International Search Report in international application PCT/US2007/016395.

* cited by examiner

*Primary Examiner* — Nicholas Lucchesi
*Assistant Examiner* — Ian Holloway
(74) *Attorney, Agent, or Firm* — Rutan & Tucker, LLP

(57) ABSTRACT

A medical needle shield apparatus having an anti-rotation component prevents the medical needle from rotating relative to a safety shield.

21 Claims, 12 Drawing Sheets

MEDICAL NEEDLE SAFETY SHIELD APPARATUS WITH AN ANTI-ROTATION MEMBER

TECHNICAL FIELD

The present invention relates generally to safety shields for medical needles, and more particularly, to safety shields that protect a needle point of a medical needle.

BRIEF DESCRIPTION OF THE DRAWINGS

Understanding that drawings depict only typical embodiments of the invention and are not therefore to be considered to be limiting of its scope, the invention will be described and explained with additional specificity and detail through the use of the accompanying drawings as listed below.

FIG. 1D shows the safety shield in its retracted position so that the needle is ready to use. As in FIG. 1C, hub cavity is shown in phantom as is the anti-rotation component.

FIG. 1F shows the safety shield in its sheathed position around the tip of the medical needle. The hub cavity is shown in phantom as is the hub end of the anti-rotation component.

Figure 1A:
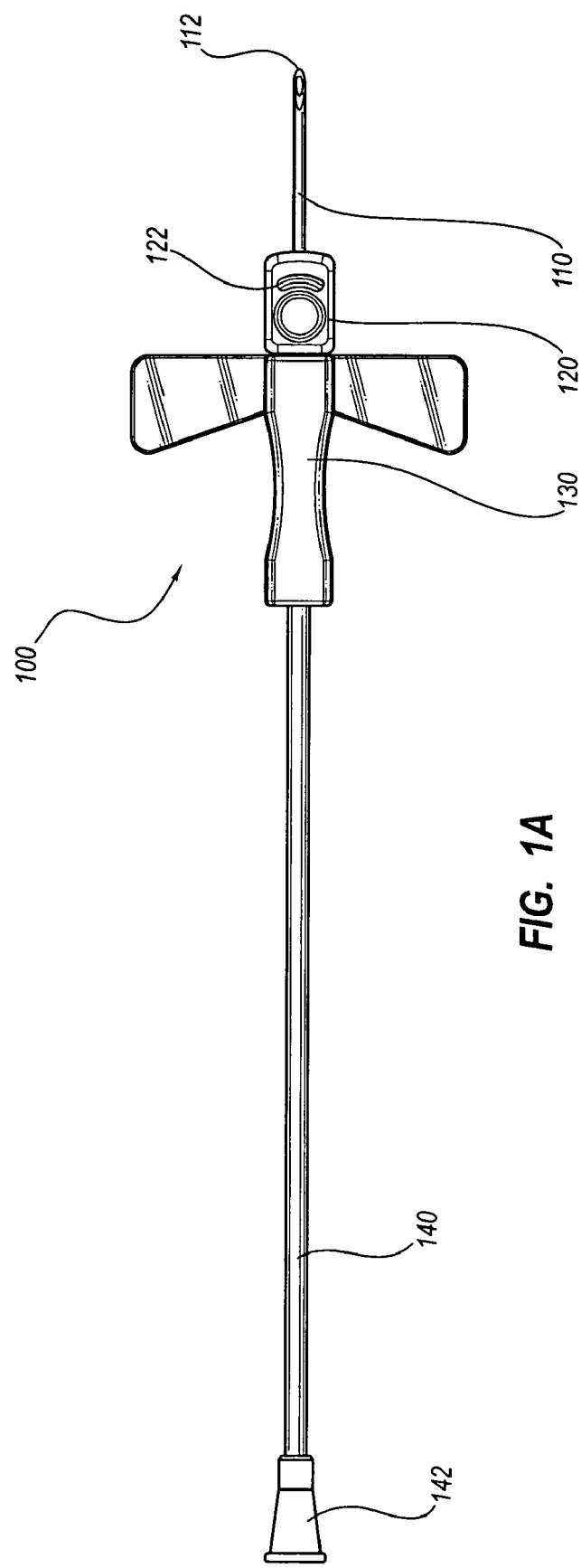
FIG. 1A is a plan view of a medical needle shield apparatus with a safety housing in its retracted position. The apparatus also shows optional tubing extending from the needle hub terminating at a fitting such as a convention luer fitting.

INDEX OF ELEMENTS IN THE DRAWINGS 100 medical needle shield apparatus
110 medical needle
112 a tip of a medical needle
120 safety housing
122 push tab
124 connector
130 needle hub
132 body of the hub
134 arms of the hub
136 hub cavity
140 tubing
142 fitting
150 binding component
170 anti-rotation component
172 shield end
174 hub end
176 hole

DETAILED DESCRIPTION OF THE EXEMPLARY EMBODIMENTS

The exemplary embodiments of the medical needle shield apparatus and methods of manufacture disclosed are discussed in terms of medical needles for infusion of intravenous fluids, medication infusion or fluid collection, guiding of other needles, e.g., biopsy, and more particularly, in terms of needle shield apparatus employed with a needle cannula that prevent hazardous exposure to the needle tip, including, for example, inadvertent needle sticks. It is envisioned that the present disclosure, however, finds application to a wide variety of cannula needles and devices for the infusion of preventive medications, medicaments, therapeutics, etc. to a subject, such as, for example, epidural needles, spinal needles, biopsy needles, chiba needles, potts cournand needles, coaxial introducer needles, Y-sites, etc. It is also envisioned that the present disclosure may be employed for collection of body fluids and/or tissues, including those employed during procedures relating to soft tissue biopsy, bone biopsy, phlebotomy, digestive, intestinal, urinary, veterinary, etc. It is contemplated that the medical needle shield apparatus may be utilized with other medical needle applications including, but not limited to, fluid infusion, fluid collection, catheters, catheter introducers, guidewire introducers, biopsy needle introducers, spinal and epidural, biopsy, aphaeresis, dialysis, blood donor, Veress needles, Huber needles, etc.

In the discussion that follows, the term "proximal" refers to a portion of a structure that is closer to a clinician, and the term "distal" refers to a portion that is further from the clinician. As used herein, the term "subject" refers to a patient that receives infusions or has blood and/or fluid collected therefrom using the medical needle shield apparatus. According to the present disclosure, the term "clinician" refers to an individual administering an infusion, performing fluid or tissue collection, installing or removing a needle cannula from a medical needle shield apparatus and may include support personnel.

The following discussion includes a description of some of the components of a medical needle shield apparatus, followed by a description of the method of manufacturing the medical needle shield apparatus in accordance with the present disclosure. Reference will now be made in detail to the exemplary embodiments of the disclosure, which are illustrated in the accompanying figures.

In the figures, like components are designated by like reference numerals throughout the several views. FIGS. 1A-1H depict an embodiment of a medical needle shield apparatus 100 having an anti-rotation component 170 which integrally extends from safety housing 120. FIGS. 2A-2D depict another embodiment of a medical needle shield apparatus 100' featuring an anti-rotation component 170' which is connected to safety housing 120. Anti-rotation component 170 prevents the safety housing 120 from rotating. Rotation of safety housing 120 is undesirable as it may result in safety housing 120 "twisting off" from needle tip 112 after safety housing is locked into its sheathed position over needle tip 112.

Figure 1B:
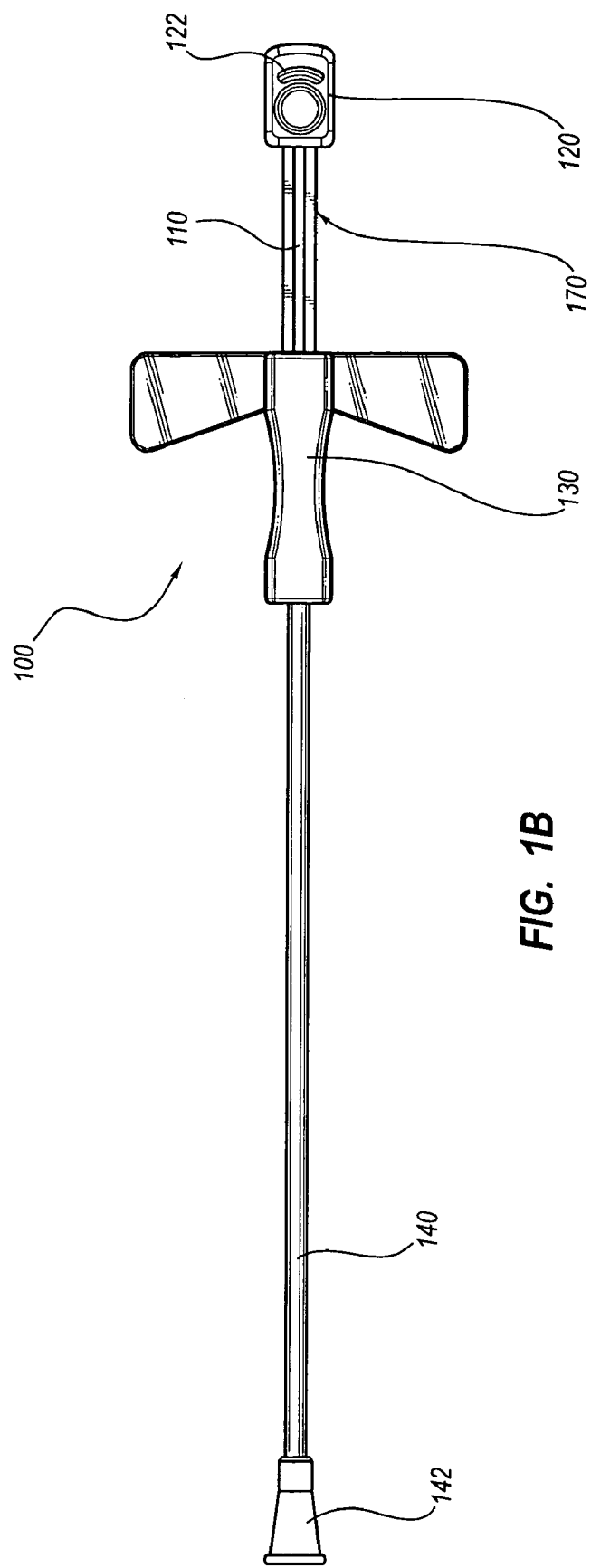
FIG. 1B is a plan view of a medical needle shield apparatus with a safety housing in its sheathed position. The apparatus also shows optional tubing extending from the needle hub terminating at a fitting such as a convention luer fitting.

FIGS. 1A-1B depict a medical needle shield apparatus 100 with safety housing 120 in its two positions. FIG. 1A shows safety housing with safety housing 120 in its retracted position. To advance safety housing 120 on medical needle 110 to its sheathed position around needle tip 112, the user depresses tab 122. FIG. 1B shows safety housing 120 in its sheathed position around needle tip 112. In the view provided by FIG. 1B, anti-rotation component 170 can be seen extending from safety housing 120 below needle 110.

In the embodiment shown in FIGS. 1A-1B, needle hub 130 is coupled to optional tubing 140 which terminates at a fitting 142 such as a convention luer fitting. Such optional components permit the medical needle shield apparatus to be used for infusion or removal of fluids.

Figure 1C:
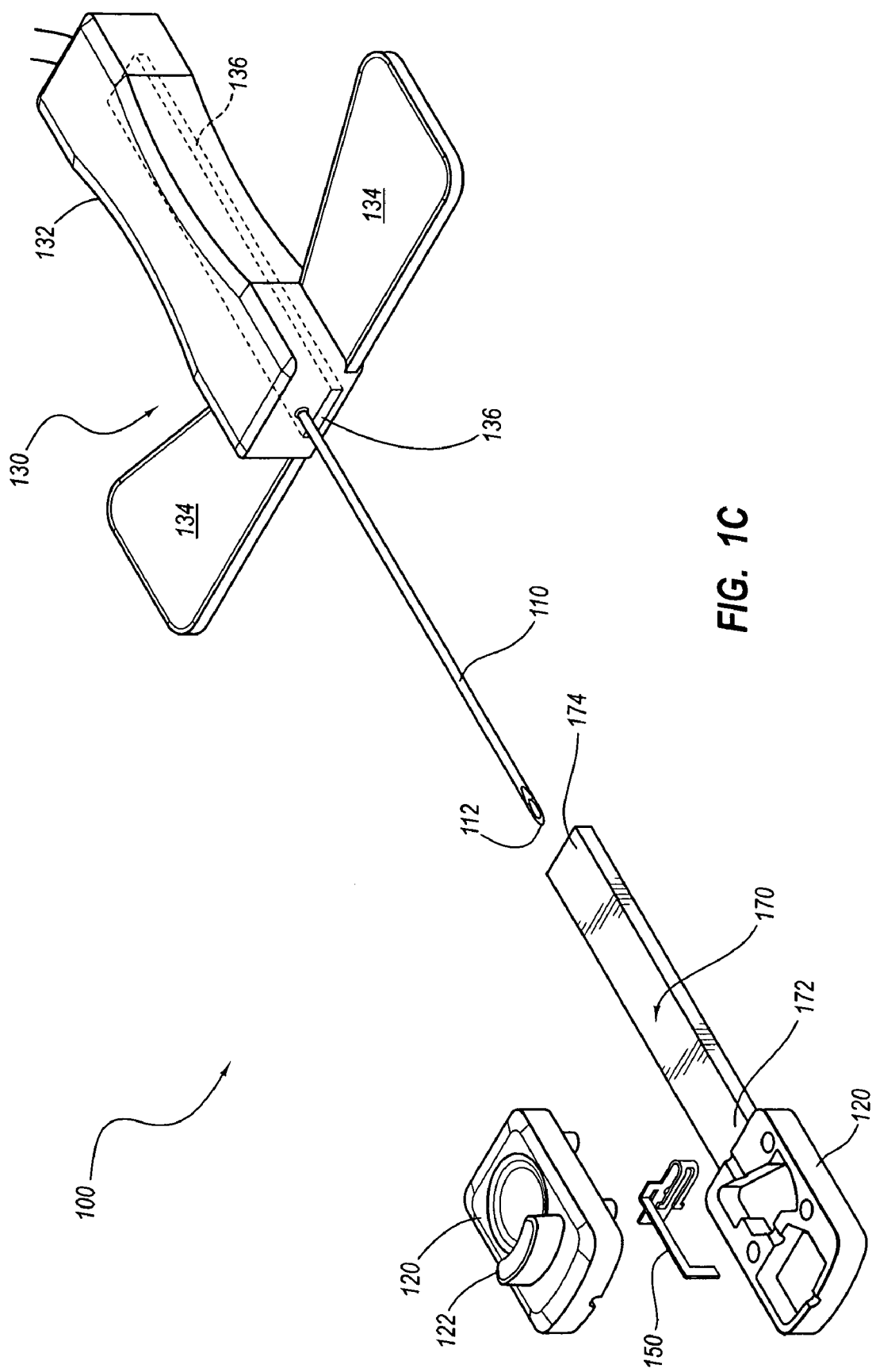
FIG. 1C is an enlarged, exploded perspective view of the medical needle shield apparatus shown in FIGS. 1A-1B with only a portion of the option tubing shown. The cavity in the hub which receives the anti-rotation component is shown in phantom.

FIG. 1C provides an enlarged, exploded perspective view of medical needle shield apparatus 100. Safety shield 120 is shown separated into two halves with binding component 150 between the two halves. Anti-rotation component 170 integrally extends from the bottom half of safety shield 120.

The anti-rotation component 170 is shown having a thin, elongated configuration with a rectangular cross-sectional shape. The thin, elongated cross-sectional shape of anti-rotation component 170 enables medical needle shield apparatus 100 to have a low-profile and securely prevents rotation of safety housing 120 on medical needle 110 both before and after safety housing 120 is locked into its sheathed position over needle tip 112. It is advantageous for medical needle shield apparatus 100 to have a low profile in many applications including but not limited to dialysis needles and winged steel needles.

Needle hub 130 has a body 132 with optional arms 134 which permit needle hub 130 to be easily grasped. Needle hub 130 also features a needle hub cavity 136 which receives anti-rotation component 170. Needle hub cavity 136 has a shape corresponding to the shape of anti-rotation component 170.

Anti-rotation component 170 and cavity 136 in hub 130 have the same cross-sectional shapes. Because they are both devoid of surface features, the fit between the anti-rotation component 170 and cavity 136 in hub 130 may be relatively tight. Anti-rotation component 170 and cavity 136 in hub 130 are both shown with a rectangular cross-section shape. However, anti-rotation component 170 and cavity 136 in hub 130 may have any other cross-sectional shape. For example, they may both have ellipsoid cross-sectional shapes.

Figure 1D:
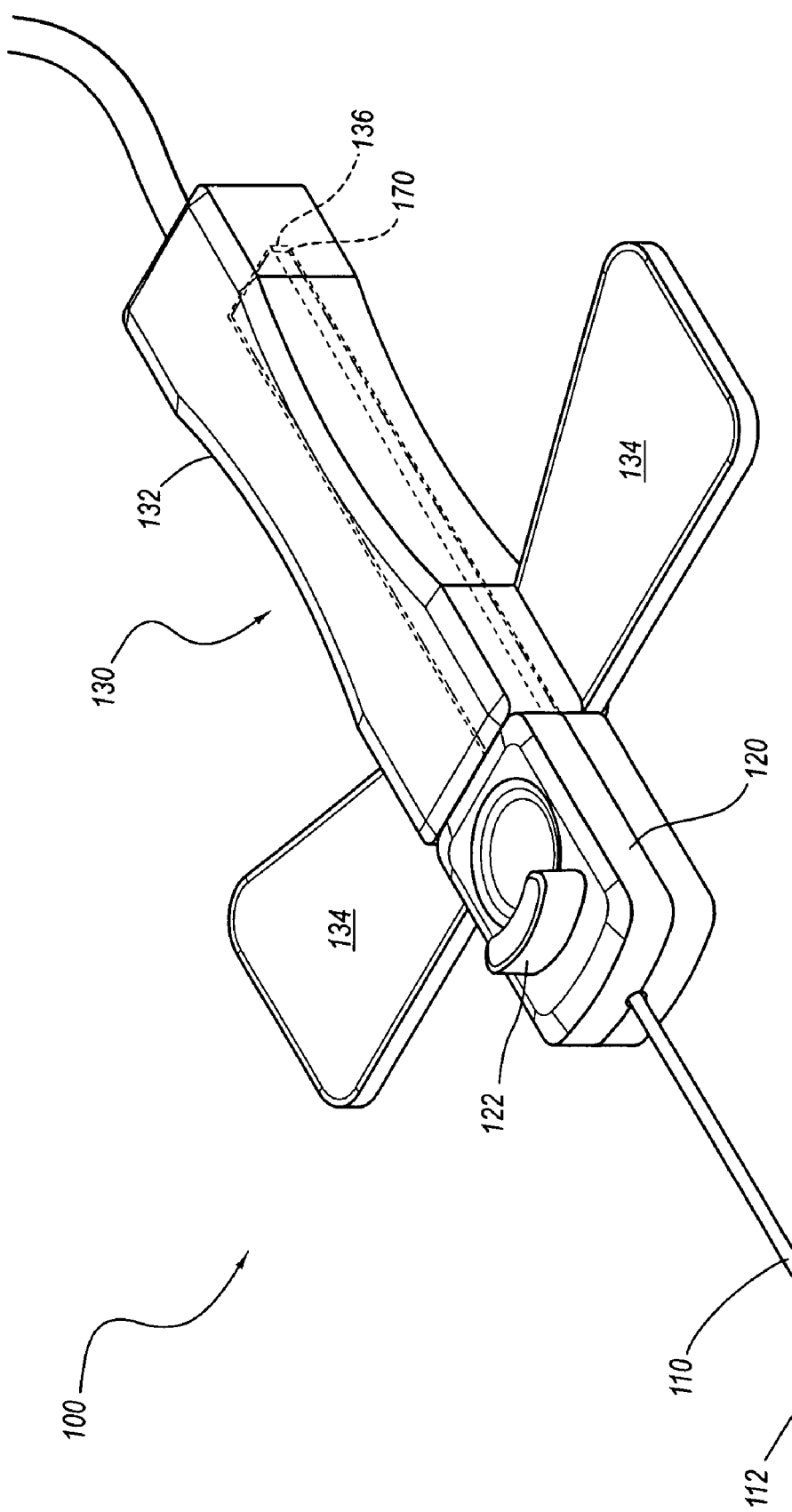
FIG. 1D is an enlarged perspective view of the medical needle shield apparatus shown in FIGS. 1A-1C.

FIG. 1D shows safety shield 120 in its retracted position so that needle 110 is ready to use and needle tip 112 is exposed. FIG. 1D also shows anti-rotation component 170 in phantom to depict its position in needle hub cavity 136. Note the thin profile of anti-rotation component 170 enables it to reside longitudinally inside the needle hub 130 when the needle device is in the retracted position without requiring needle hub 130 to a bulky profile. Also, cavity 136 has a length corresponding to at least the length of anti-rotation component 170 as it extends beyond safety housing 120 so that anti-rotation component 170 is not visible when safety housing 120 is in retracted position. Because anti-rotation component 170 is tucked away so that it is not visible, the anti-rotation component does not make apparatus 100 cumbersome to use.

Figure 1E:
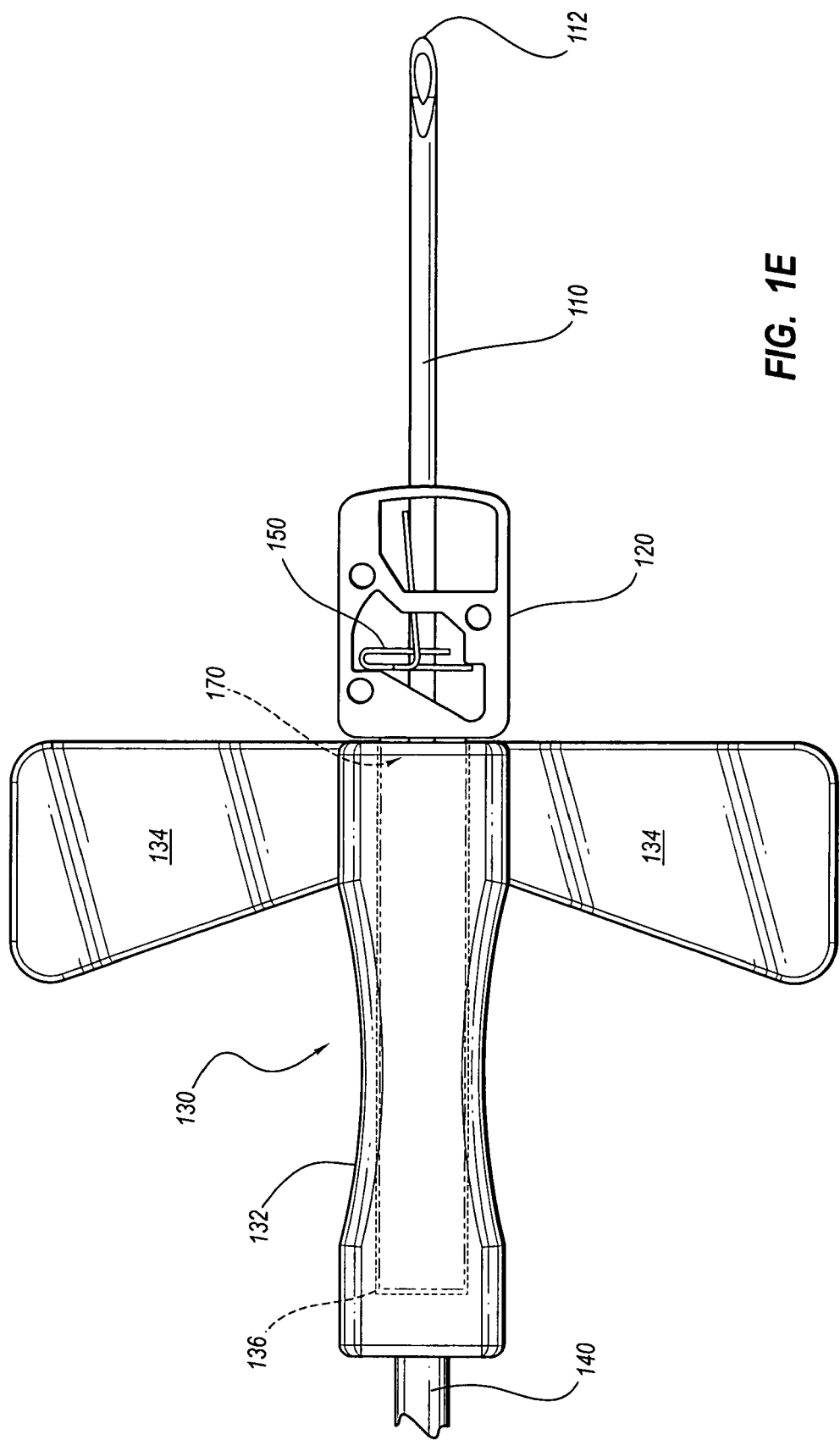
FIG. 1E is a cross-sectional view of the safety shield in its retracted position. This view shows the configuration of the binding component in the safety shield.

FIG. 1E provides a cross-sectional view of safety shield 120 in its retracted position to expose the configuration of binding component 150. Binding component 150 allows needle 110 to move through safety shield 120 until encountering or sensing needle tip 112 as shown in FIG. 1G-1H which causes binding component 150 to pivot into a binding or locking position. Pivoting of binding component 150 causes it to lock against needle 110 so that safety shield 120 remains around needle tip 112.

Binding component 150 is an exemplary binding component and other similar binding components can be used. Binding components are also referred to as binding members, spring clips, friction based plates, etc. Examples of these components and other configurations for safety shields are disclosed in U.S. patent application Ser. No. 10/721,526 titled Resettable Safety Shield for Medical Needles which was filed on Nov. 25, 2003 and was published as U.S. Patent Publication No. 2004/0078003; International Patent Application No. PCT/US2004/039400 which was filed on Nov. 23, 2004 and was published as International Publication No. WO 2005/053774 on Jun. 16, 2005; PCT Application No. PCT/US04/10800 filed on Nov. 23, 2004 by Snow et al., U.S. patent application Ser. No. 10/739,868 filed on Dec. 18, 2003 by Ferguson et al., U.S. patent application Ser. No. 10/721,526 filed on Nov. 25, 2003 by Ferguson et al., U.S. patent application Ser. No. 10/409,819 filed on Apr. 8, 2003 by Ferguson et al., and U.S. patent application Ser. No. 10/322,288 filed on Dec. 17, 2002 by Ferguson et al., U.S. patent application Ser. No. 10/202,201 filed on Jul. 23, 2002 by Ferguson et al., and U.S. patent application Ser. No. 09/809,357 filed on Mar. 15, 2001 by Ferguson et al. These patent applications and the patents which issue from them are hereby incorporated by reference.

Figure 1F:
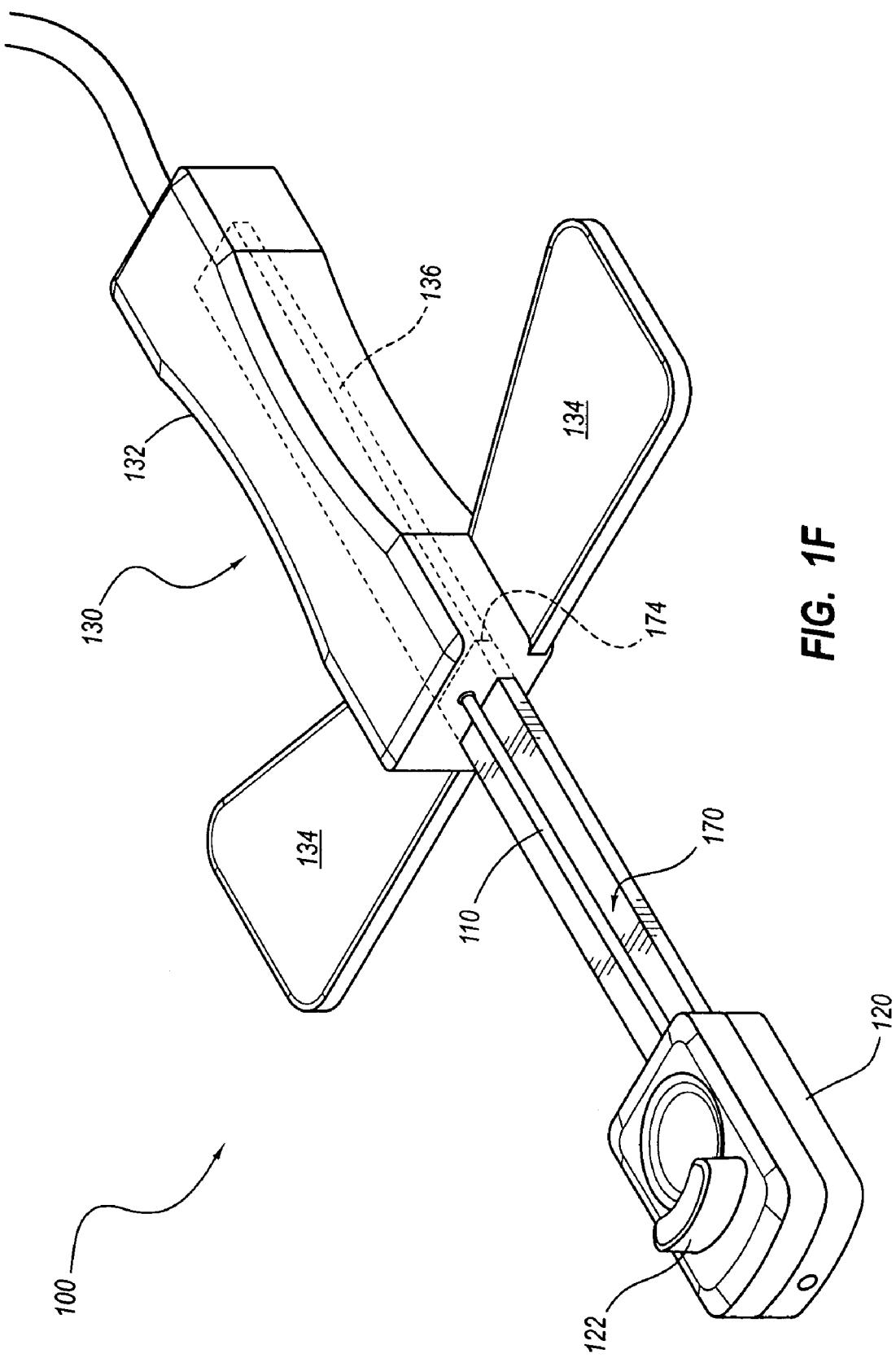
FIG. 1F is an enlarged perspective view of the medical needle shield apparatus shown in FIGS. 1A-1E.
Figure 1G:
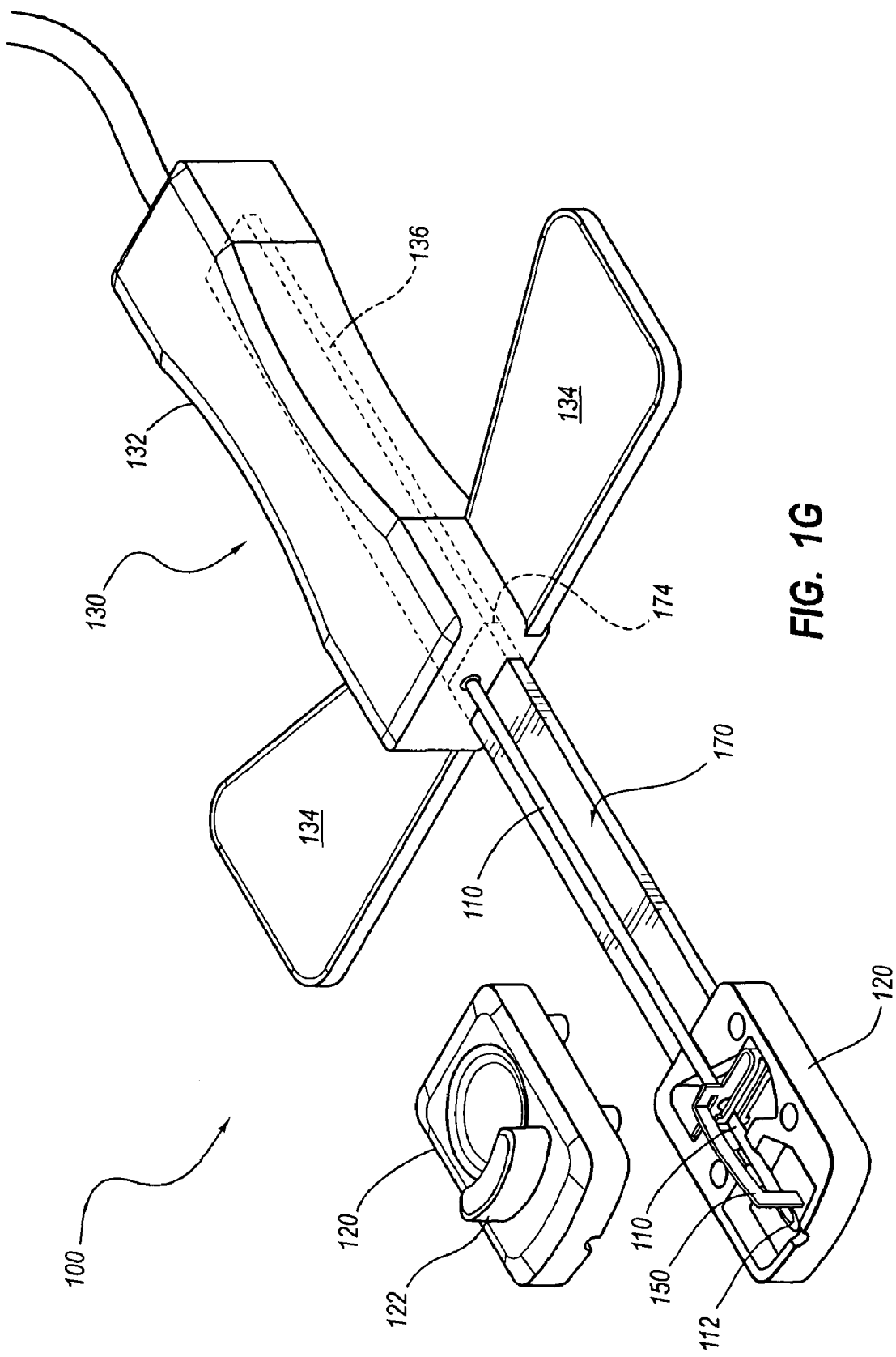
FIG. 1G is partially exploded perspective view of the medical needle shield apparatus shown in FIGS. 1A-1F. As in FIG. 1F, the safety shield is in its sheathed position.
Figure 1H:
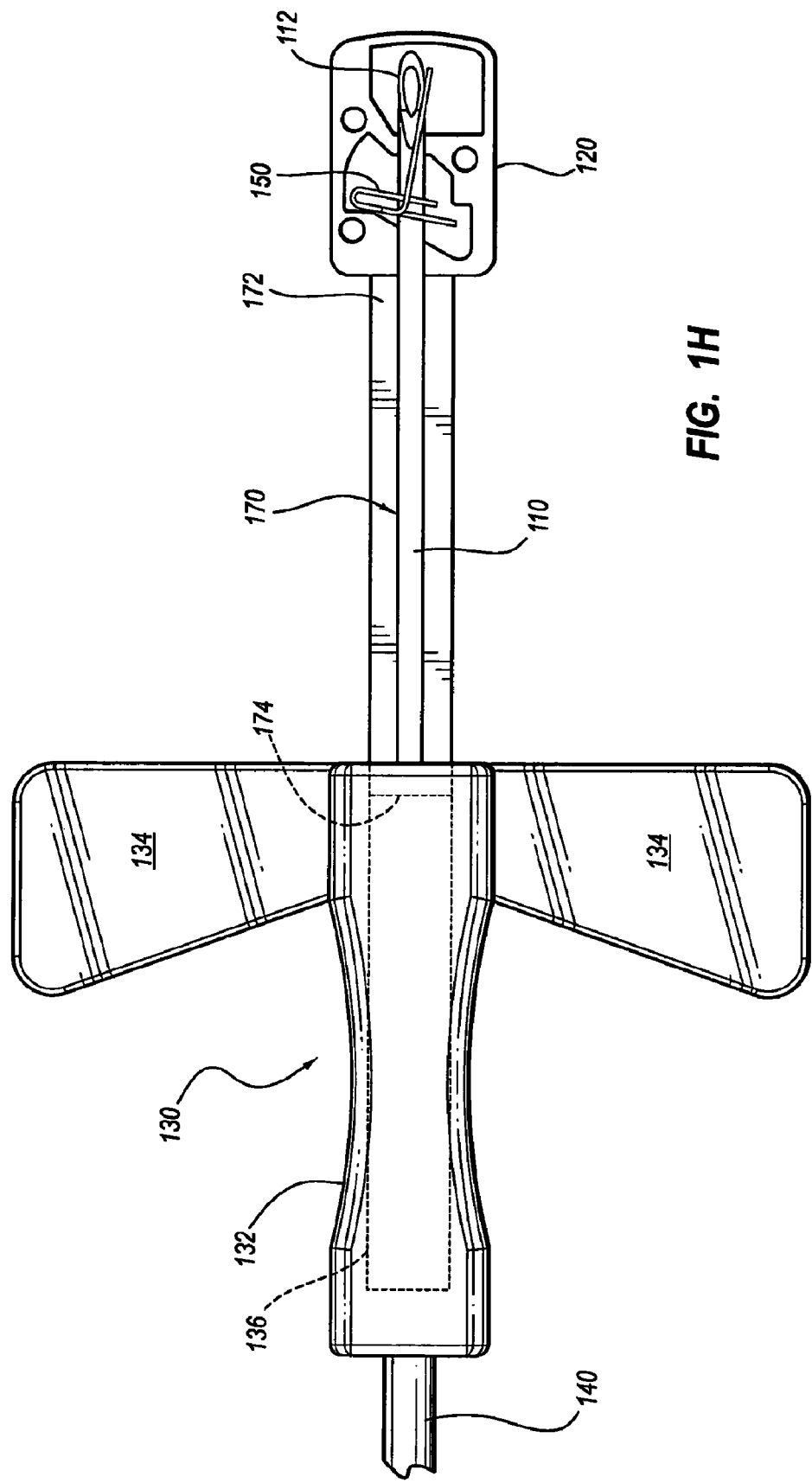
FIG. 1H is a cross-sectional view of the safety shield in its sheathed position. This view shows the configuration of the binding component when in its locked position on the medical needle.

As shown in FIGS. 1F-1H, after medical needle 110 has been used in a procedure and during safety housing lockout, anti-rotational component 170 extends forward with the safety housing 120 over the needle tip 112. FIGS. 1G-1H show binding component 150 locked about needle 110 with safety housing 150 parked over needle tip 112 to provide increased protection from accidental needle sticks and to prevent continued forward motion of safety housing 120 along needle 110. In this sheathed position, anti-rotational component 170 inhibits rotation or twisting of safety housing 120 to maintain protection of needle tip 112.

In the transition between the retracted position of safety shield 120 shown in FIGS. 1A and 1D-1E and the sheathed position shown in FIGS. 1B and 1G-1H, anti-rotational component 170 moves forward with safety housing 120 while at least a portion of anti-rotational component 170 remains within needle hub 130. The portion of anti-rotation component 170 extending into needle hub cavity 136 is not directly connected to the needle hub 130 and is not designed as a stopping or retaining mechanism to limit the movement of the safety housing 120 as it moves forward.

Anti-rotation component 170 is depicted in FIGS. 1A-1H with no features other than its shape. In particular, anti-rotation component 170 is devoid of any features which tether it to hub 130 or which lock its movement relative to hub 130. Because it is not necessary for anti-rotation component to feature configurations which enable it to do anything besides prevent rotation of safety shield 120 relative to needle 100, anti-rotation component 170 has a cross-sectional shape which corresponds along its entire length with the cross-sectional shape of cavity 136 in hub 130.

Anti-rotation component 170 is prevented from coming out of cavity 136 due to the length of needle 110. More particularly, the length of anti-rotation component 170 extending beyond safety housing 120 is greater than the length of the portion of needle 110 extending from hub 130 so that the hub end 174 of anti-rotation component 174 remains in cavity 136 of hub 130 when safety housing 120 sheathes tip 112 of medical needle 110. Note also that at least the majority of the length of anti-rotation component 170 extending beyond safety housing 120 is positioned in cavity 136 in hub 130 when safety housing 120 is in the retracted position. This configuration permits the apparatus to have a low profile.

Figure 2A:
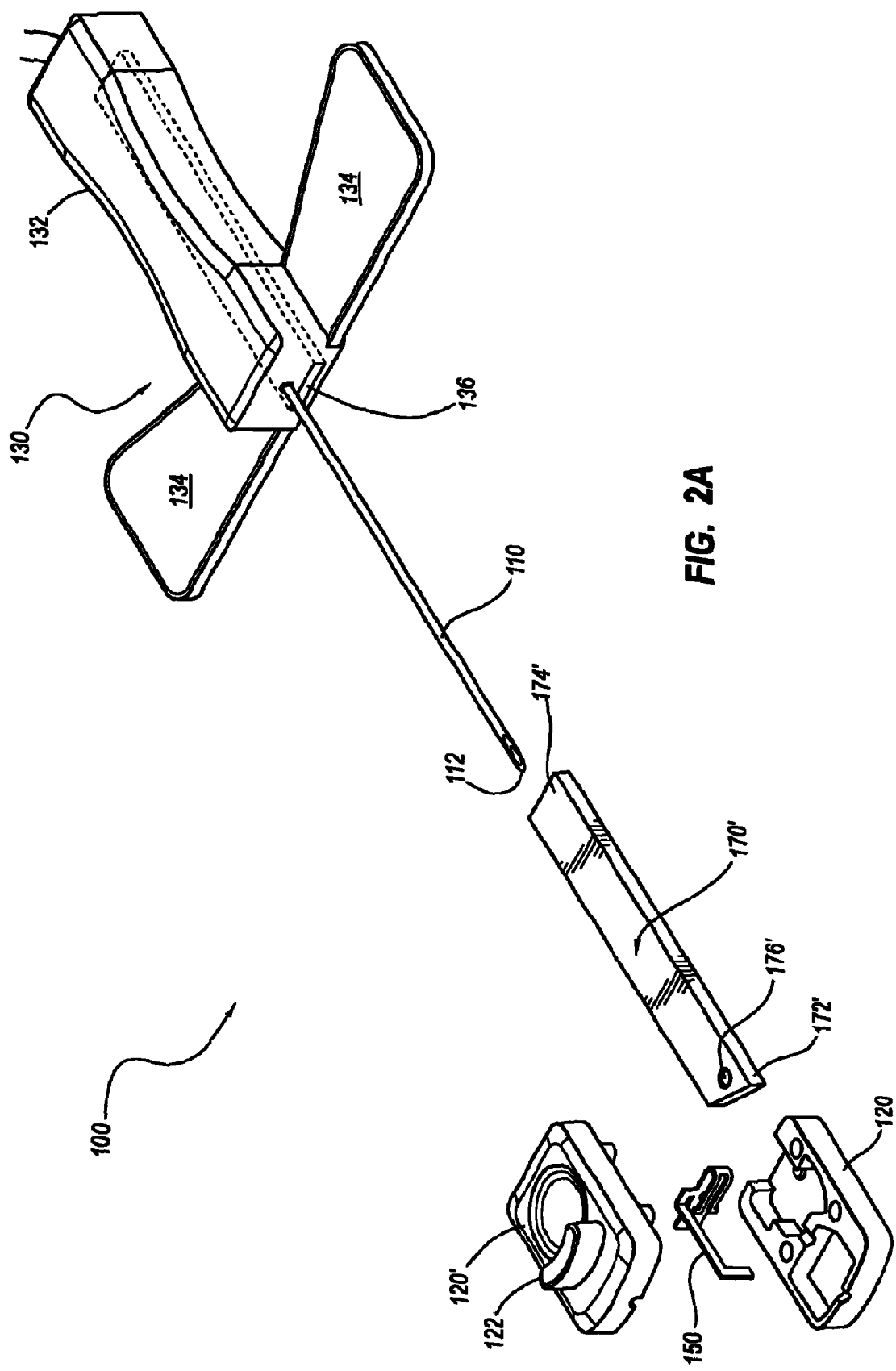
FIG. 2A is an exploded perspective view of another embodiment of the medical needle shield apparatus. In contrast to the anti-rotation component of the embodiment depicted in FIGS. 1A-1H, the anti-rotation component is connected to the safety shield and is not integral with the safety shield.
Figure 2B:
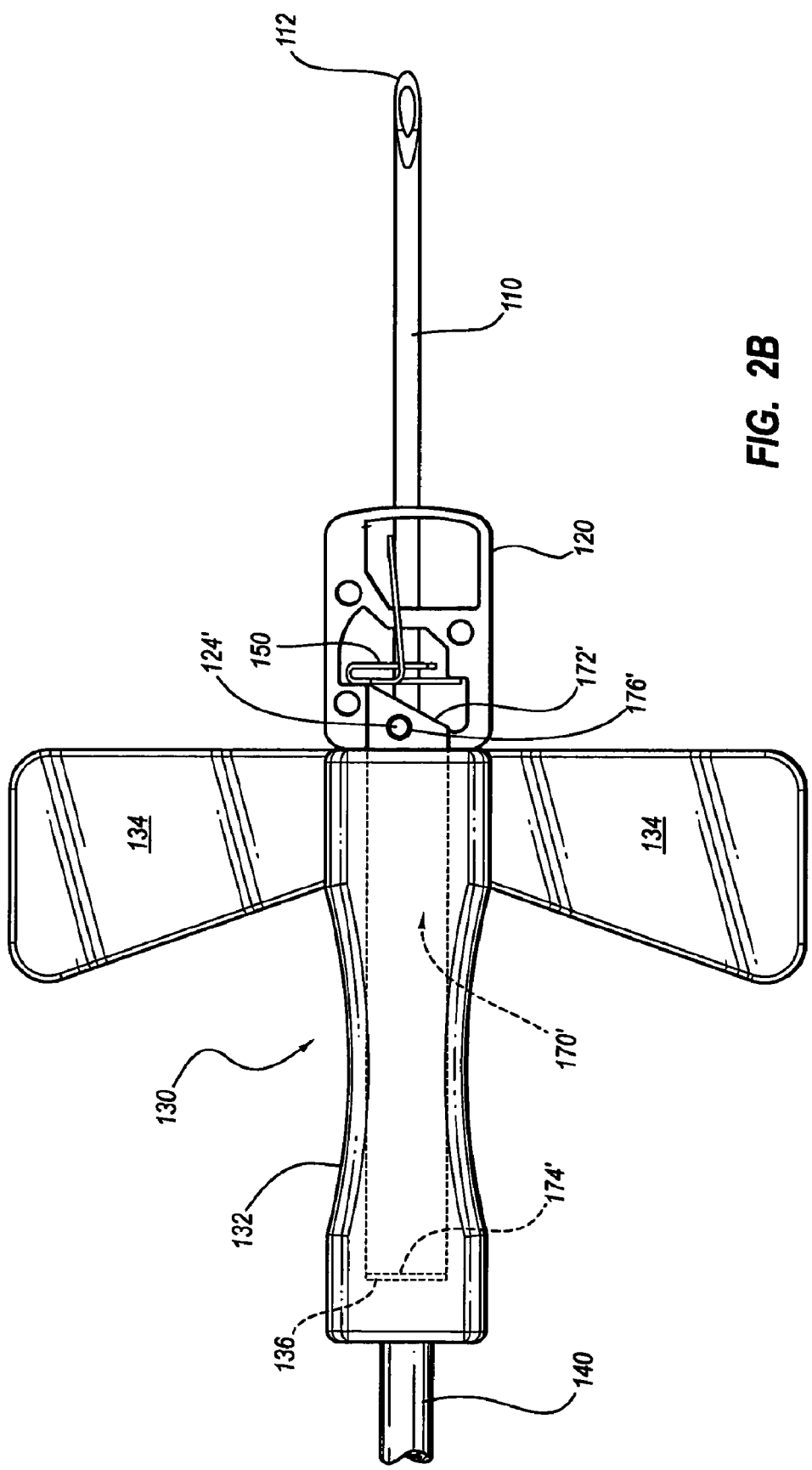
FIG. 2B is a cross-sectional view of the safety shield in its retracted position of the embodiment shown in FIG. 2A. This view shows the configuration of the binding component in the safety shield while positioned to permits the safety shield to move relative to the needle.
Figure 2C:
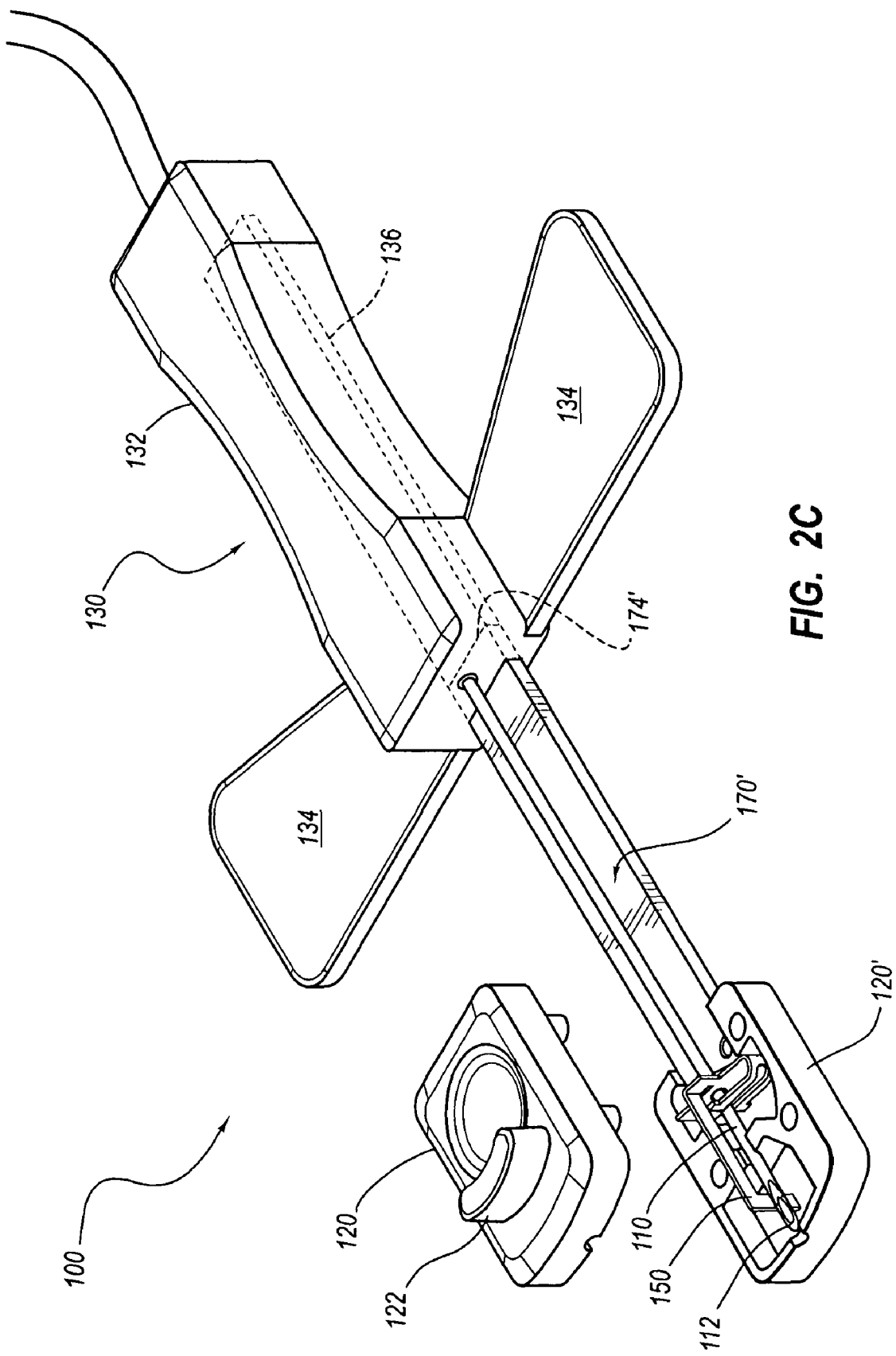
FIG. 2C is partially exploded perspective view of the medical needle shield apparatus shown in FIGS. 2A-2B. The safety shield is in its sheathed position.
Figure 2D:
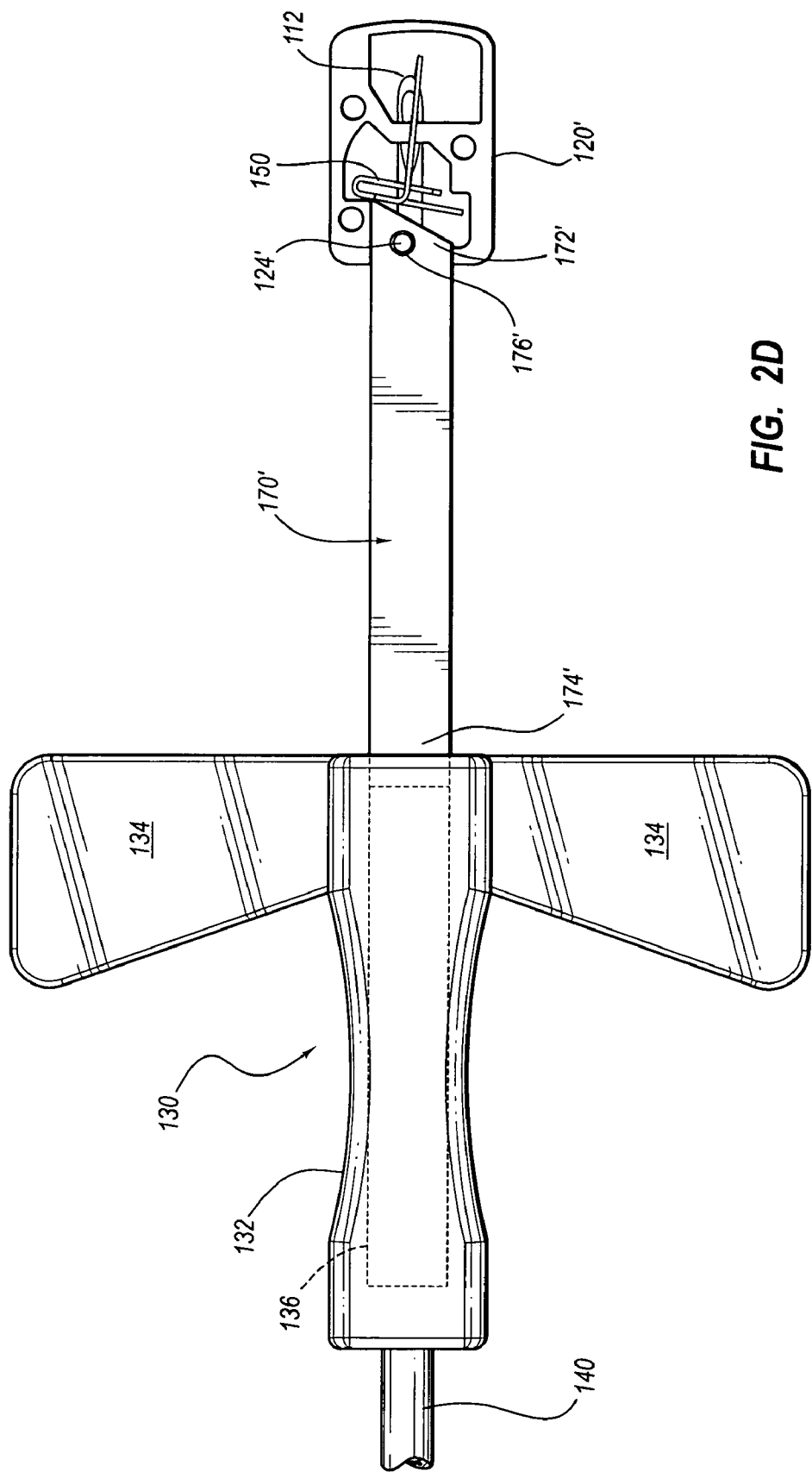
FIG. 2D is a cross-sectional view of the safety shield in its sheathed position. This view shows the configuration of the binding component when in its locked position on the medical needle. This view also shows the connector of the safety shield extending through the hole of the anti-rotation component.

FIG. 2A provides an exploded perspective view of medical needle shield apparatus 100'. As shown, anti-rotation component 170' does not extend integrally from safety housing 120'. All of the other components of medical needle shield apparatus 100' are identical to those of medical needle shield apparatus 100. FIGS. 2B-2C show safety housing 120' respectively in its retracted position and sheathed position. While these views show that anti-rotation component 170' is connected to safety housing 120', the connection is best seen in FIG. 2D which shows needle tip 112 sheathed within safety housing 120'.

The safety shields disclosed herein are examples of means for sheathing the tip of the medical needle. The anti-rotation components disclosed herein are examples of means for preventing the rotation of the sheathing means relative to the medical needle. The binding components disclosed herein are examples comprising means for locking movement between the sheathing means and the medical needle when the sheathing means encounters the needle tip.

The above description fully discloses the invention including preferred embodiments thereof. Without further elaboration, it is believed that one skilled in the art can use the preceding description to utilize the invention to its fullest extent. Therefore the examples and embodiments disclosed herein are to be construed as merely illustrative and not a limitation of the scope of the present invention in any way.

It will be apparent to those having skill in the art that changes may be made to the details of the above-described embodiments without departing from the essential characteristics and underlying principles of the invention. Embodiments of the invention in which an exclusive property or privilege is claimed are defined as follows. Note that elements recited in means-plus-function format are intended to be construed in accordance with 35 U.S.C. §112 ¶6.

The invention claimed is:

1. A medical needle shield apparatus comprising:
    a medical needle extending from a hub and terminating at a tip,
    a safety housing on the medical needle which is moveable to a sheathed position to sheath the tip of the medical needle, the safety housing including a binding component positioned around the needle, the binding component comprising a single spring clip including first and second linear portions forming a guide slot through which the needle is positioned, the binding component pivoting into a locking position upon encountering the needle tip, and
    an anti-rotation component extending from the safety housing such that the safety housing and anti-rotation component move together while preventing the safety housing from rotating with respect to the medical needle, wherein a body of the hub has a cavity with a cross-sectional shape configured to receive the anti-rotation component, and wherein the anti-rotation component is movably positioned in the cavity, wherein the anti-rotation component and the hub are configured to not lock with each other when the safety housing is moved to the sheathed position.

2. The apparatus of claim 1, wherein the anti-rotation component terminates at a hub end which is movably positioned in the cavity.

3. The apparatus of claim 1, wherein the length of the anti-rotation component extending beyond the safety housing is greater than the length of the needle extending from the hub so that a hub end of the anti-rotation component remains in the cavity of the hub when the safety housing sheathes the tip of the medical needle.

4. The apparatus of claim 1, wherein the cavity has a length corresponding to at least the length of the anti-rotation component extending beyond the safety housing so that the anti-rotation component is not visible when the safety housing is in retracted position.

5. The apparatus of claim 1, wherein the anti-rotation component has a cross-sectional shape which corresponds along its entire length with the cross-sectional shape of the cavity in the hub.

6. The apparatus of claim 1, wherein the anti-rotation component and the cavity in the hub have the same cross-sectional shapes.

7. The apparatus of claim 1, wherein the anti-rotation component and the cavity in the hub each have rectangular cross-sectional shapes.

8. The apparatus of claim 1, wherein the anti-rotation component is devoid of any features which tether the anti-rotation component to the hub.

9. The apparatus of claim 1, wherein the anti-rotation component extends integrally from the safety housing.

10. The apparatus of claim 1, wherein the anti-rotation component is connected to the safety housing.

11. A medical needle shield apparatus comprising:
    a medical needle extending from a hub and terminating at a tip,
    a safety housing which is moveable on the medical needle from a retracted position to a sheathed position with respect to the tip of the medical needle, the safety housing including a binding component positioned around the needle, the binding component comprising a single spring clip that senses the needle tip, locks the needle, and sheaths the needle tip, the binding component pivoting into a locking position upon encountering the needle tip, the binding component further including first and second linear portions forming a guide slot through which the needle is positioned, the spring clip, and
    an anti-rotation component extending from the safety housing such that the safety housing and anti-rotation component move together while preventing the safety housing from rotating with respect to the medical needle,
    wherein at least the majority of the length of the anti-rotation component extending beyond the safety housing is positioned in a cavity in a body of the hub when the safety housing is in the retracted position, and wherein the anti-rotation component and the hub are configured not to lock with each other when the safety housing is moved to the sheathed position.

12. The apparatus of claim 11, wherein the anti-rotation component terminates at a hub end, and wherein the length of the anti-rotation component extending beyond the safety housing is greater than the length of the needle extending from the hub so that the hub end of the anti-rotation component remains in the cavity of the hub when the safety housing is in the sheathed position.

13. The apparatus of claim 11, wherein the cavity has a length corresponding to at least the length of the anti-rotation component extending beyond the safety housing so that the anti-rotation component is not visible when the safety housing is in retracted position.

14. The apparatus of claim 11, wherein the anti-rotation component has a cross-sectional shape which corresponds along its entire length with the cross-sectional shape of the cavity in the hub.

15. The apparatus of claim 11, wherein the anti-rotation component and the cavity in the hub have the same cross-sectional shapes.

16. The apparatus of claim 11, wherein the anti-rotation component and the cavity in the hub each have rectangular cross-sectional shapes.

17. The apparatus of claim 11, wherein the anti-rotation component is devoid of any features which tether the anti-rotation component to the hub.

18. The apparatus of claim 11, wherein the anti-rotation component extends integrally from the safety housing.

19. The apparatus of claim 11, wherein the anti-rotation component is connected to the safety housing.

20. A medical needle shield apparatus comprising:
a medical needle extending from a hub and terminating at a tip,
means for sheathing the tip of the medical needle, including a binding means positioned around the needle allowing the medical needle to move through the means for sheathing until encountering the needle tip which causes the binding means to pivot into a locking position, the binding means comprising a single spring clip that senses the needle tip, locks the needle, and sheaths the needle tip, the binding means further including first and second linear portions forming a guide slot through which the needle is positioned, the spring clip, and
means for preventing the rotation of the sheathing means relative to the medical needle, wherein the means for preventing rotation and the hub are configured to not lock with each other when the means for sheathing the tip sheaths the tip, and wherein the means for preventing rotation is positioned in a hub body cavity.

21. The apparatus of claim 20, further comprising means for locking movement between the sheathing means and the medical needle when the sheathing means encounters the needle tip.

* * * * *